United States Patent
San et al.

(10) Patent No.: US 8,962,272 B2
(45) Date of Patent: Feb. 24, 2015

(54) ENGINEERED BACTERIA PRODUCE SUCCINATE FROM SUCROSE

(75) Inventors: Ka-Yiu San, Houston, TX (US); George N. Bennett, Houston, TX (US); Jian Wang, Changchun (CN)

(73) Assignee: William Marsh Rice University, Houston, TX (US)

( * ) Notice: Subject to any disclaimer, the term of this patent is extended or adjusted under 35 U.S.C. 154(b) by 49 days.

(21) Appl. No.: 13/696,465

(22) PCT Filed: Jun. 20, 2011

(86) PCT No.: PCT/US2011/041074
§ 371 (c)(1),
(2), (4) Date: Nov. 6, 2012

(87) PCT Pub. No.: WO2011/163128
PCT Pub. Date: Dec. 29, 2011

(65) Prior Publication Data
US 2013/0052705 A1    Feb. 28, 2013

Related U.S. Application Data

(60) Provisional application No. 61/356,909, filed on Jun. 21, 2010.

(51) Int. Cl.
C12P 1/00      (2006.01)
C12P 21/06     (2006.01)
C12P 7/40      (2006.01)
C12P 7/46      (2006.01)
C12N 1/20      (2006.01)

(52) U.S. Cl.
CPC ........... *C12P 7/46* (2013.01); *C12Y 604/01001* (2013.01)
USPC ............ 435/41; 435/69.1; 435/136; 435/145; 435/252.33

(58) Field of Classification Search
None
See application file for complete search history.

(56) References Cited

U.S. PATENT DOCUMENTS

| | | | |
|---|---|---|---|
| 4,806,480 | A  | 2/1989  | Lopez |
| 6,743,610 | B2 | 6/2004  | Donnelly et al. |
| 7,569,380 | B2 | 8/2009  | San et al. |
| 7,790,416 | B2 | 9/2010  | San et al. |
| 7,927,859 | B2 | 4/2011  | San et al. |
| 7,935,511 | B2 | 5/2011  | San et al. |
| 2006/0073577 | A1 | 4/2006 | Ka-Yiu et al. |
| 2006/0141594 | A1 | 6/2006 | San et al. |
| 2007/0249028 | A1 | 10/2007 | San et al. |

FOREIGN PATENT DOCUMENTS

WO           2008030995        3/2008
WO  PCT/US2011/041074         10/2011

OTHER PUBLICATIONS

Cowan et al. (Characterization of the Major Promoter for the Plasmid-Encoded Sucrose Genes scrY, scrA, and scrB, Journal of Bacteriology, Dec. 1991, p. 7464-7470 vol. 173, No. 23).*
Bruschi et al. (Biotechnology Advances 30 (2012) 1001-1010).*
Garcia et al. (Mol Gen Genet (1985) 201 : 575-577).*
Wohlieter et al. (J. Bacteriol. 1975, 122(2):401).*
Bogs et al, "Molecular analysis of sucrose metabolism of *Erwinia amylovora* and influence on bacterial virulence," J. Bacteriol., 182(19), 2000, pp. 5351-5358.
Andersson C., et al. (2007) Effect of different carbon sources on the production of succinic acid using metabolically engineered *Escherichia coli*, Biotechnol. Prog. 23: 381-388.
Blankschien M.D., et al. (2010) Metabolic engineering of *Escherichia coli* for the production of succinate from glycerol, Metab. Eng. 12: 409-419.
Cox, S.J. (2006) Development of a metabolic network design and optimization frame work incorporating implementation constraints: A succinate production case study, Metab. Eng. 8: 46-57.
Datsenko, Ka, BL Wanner (2000) One-step inactivation of chromosomal genes in *Escherichia coli* K-12 using PCR products. Proc. Natl. Acad. Sci. U.S.A. 97(12):6640-5.
D.W. Penfold and L.E Macaskie (2004) Production of H2 from sucrose by *Escherichia coli* strains carrying the pUR400 plasmid, which encodes invertase activity, Biotechnology Letters 26(24): 1879-1883.
Wang J., et al. (2011) Succinate production from different carbon sources under anaerobic conditions by metabolic engineered *Escherichia coli* strains, Metabolic Engineering 13: 328-335.
Wang J., et al. (2011) Succinate production from Sucrose by Metabolic Engineered *Escherichia coli* Strains under Aerobic Conditions, Biotechnol Prog. Sep.-Oct. 2011; 27(5), pp. 1242-1247.
Isar J., et al. (2007) A statistical approach to study the interactive effects of process parameters on succinic acid production from *Bacteroides fragilis*. Anaerobe13: 50-56.
Lee P.C., et al. (2003) Batch and continuous cultures of *Mannheimia succiniciproducens* MBEL55E for the production of succinic acid from whey and corn steep liquor. Bioprocess Biosyst. Eng. 26: 63-67.
Lin H., et al. (2004) Increasing the acetyl-CoA pool in the presence of overexpressed phosphoenolpyruvate carboxylase or pyruvate carboxylase enhances succinate production in *Escherichia coli*, Biotechnol. Prog. 20: 1599-1604.
Henry Lin, et al. (2005) Chemostat culture characterization of *Escherichia coli* mutant strains metabolically engineered for aerobic succinate production: a study of the modified metabolic network based on metabolite profile, enzyme activity, and gene expression profile. Metabolic Engineering 7(5-6): 337-352.
Okino S., et al. (2005) Production of organic acids by *Corynebacterium glutamicum* under oxygen deprivation. Appl. Microbiol. Biotechnol. 68: 475-480.

(Continued)

*Primary Examiner* — Suzanne M Noakes
*Assistant Examiner* — Jae W Lee
(74) *Attorney, Agent, or Firm* — Boulware & Valoir (57) ABSTRACT

Bacteria optimized to produce succinate and other feedstocks by growing on low cost carbon sources, such as sucrose.

17 Claims, 6 Drawing Sheets

(56) References Cited

OTHER PUBLICATIONS

Singh A., et al. (2011) Manipulating redox and ATP balancing for improved production of succinate in *E. coli*, Metab. Eng. 13: 76-81.

Samuelov, N.S., et al. (1991) Influence of CO2—HCO3+ levels and pH on growth, succinate production and enzyme activities of *Anaerobiospirillum succiniciproducens*, Appl. Environ. Microbiol. 57: 3013-3019.

Sanchez, A.M., et al. (2005a) Efficient succinate production from glucose through overexpression of pyruvate carboxylase in an *Escherichia coli* alcohol dehydrogenase and lactate dehydrogenase mutant, Biotechnol. Prog. 21: 358-365.

Sanchez, A.M., et al. (2005b) Novel pathway engineering design of the anaerobic central metabolic pathway in *E. coli* to increase succinate yield and productivity, Metab. Eng. 7: 229-239.

Sanchez A.M., et al. (2006) Batch culture characterization and metabolic flux analysis of succinate producing *Escherichia coli* strains, Metab. Eng. 8: 209-226.

Schmid K, et al. (1988) Plasmid mediated sucrose metabolism in *Escherichia coli* K-12: Mapping of the scr genes of pUR400. Mol Microbiol. 2: 1-8.

* cited by examiner

ENGINEERED BACTERIA PRODUCE SUCCINATE FROM SUCROSE

CROSS-REFERENCE TO RELATED APPLICATIONS

This invention is a National Filing under 35 U.S.C. §371 of International Application PCT/US11/41074, filed on Jun. 20, 2011, which claims priority to U.S. Ser. No. 61/356,909 filed Jun. 21, 2010. Each of these patent applications is incorporated by reference in its entirety.

STATEMENT REGARDING FEDERALLY SPONSORED RESEARCH OR DEVELOPMENT

Not applicable.

BACKGROUND OF THE INVENTION

The detrimental prospects of climate change, environmental damage and our dependency on diminishing fossil fuels resources is driving our society to develop methods for the manufacture of fuels and chemicals from renewable resources. Such renewable resources include crops, grasses, wood waste, bacteria, algae, and the like, and can generally be referred to as biomass. The use of renewable biomass resources has the potential to reduce our negative impact on the planet and to improve our sustainability.

Bacteria are of particular interest as a biomass resource because mankind has been experimenting with fermentation processes, such as those used to make beer, for three thousand years. Thus, large-scale fermentation culture technology is quite well developed. Additionally, the very first organism to be genetically engineered was *E. coli*, and with 40 years of recombinant DNA technology experience, the techniques for manipulating bacterial genomes are now quite reliable. Finally, the small size of bacterial genomes has allowed us to completely sequence a large variety of bacterial genomes, thus gaining insight into their metabolism and allowing us to readily manipulate their genomes and biochemical pathways. All of these factors make bacteria an attractive organism for the manufacture of specialty chemicals, such as dicarboxylic acids and their derivatives.

The small dicarboxylic acids that have 6 or fewer carbons are commercially significant chemicals with many uses. For example, the small diacids include 1,4-diacids, such as succinic acid, malic acid, and tartaric acid, and the 5-carbon molecule itaconic acid. Other diacids include the two carbon oxalic acid, three carbon malonic acid, five carbon glutaric acid and the 6 carbon adipic acid and there are many derivatives of such diacids as well.

As a group the small diacids have some chemical similarity and their uses in polymer production can provide specialized properties to the resin. Such versatility enables them to fit into the downstream chemical infrastructure markets easily. For example, the 1,4-diacid molecules fulfill many of the uses of the large scale chemical maleic anhydride in that they are converted to a variety of industrial chemicals (tetrahydrofuran, butyrolactone, 1,4-butanediol, 2-pyrrolidone and the succinate derivatives succindiamide, succinonitrile, diaminobutane and esters of succinate). Tartaric acid has a number of uses in the food, leather, metal and printing industries. Itaconic acid forms the starting material for production of 3-methylpyrrolidone, methyl-BDO, methyl-THF and others.

In particular, succinic acid or succinate—these terms are used interchangeably herein—has drawn considerable interest because it has been used as a precursor of many industrially important chemicals in the food, chemical and pharmaceutical industries. In fact, a report from the U.S. Department of Energy reports that succinic acid is one of 12 top chemical building blocks manufactured from biomass. Thus, the ability to make diacids in bacteria would be of significant commercial importance.

In fact, it is already possible to make succinate in a variety of bacteria and single cell eukaryotes, including *Actinobacillus succinogenes* (Guettler 1996), *Anaerobiospirillum succiniciproducens* (Samuelov 1991), *Bacteroides fragilis* (Isar 2007), *Corynebacterium glutamicum* (Okino 2005), *Mannheimia succiniciproducens* (Lee 2003), and *Saccharomyces cerevisiae* (Raab 2010).

Although the above microorganisms are useful, there is a strong preference for using *E. coli* in the industry due to its ease of genetic manipulation, fast growth, rate and growth on low cost culture medium. Efforts have been successful in engineering bacteria to increase their production of small diacids, such as succinate and the like. U.S. Pat. Nos. 7,569,380, 7,790,416, WO2008030995, U.S. Pat. Nos. 7,935,511, 7,927,859 and US2006073577 describe some of our efforts in that regard, and many other laboratories and companies have also had success (Cox 2006, Singh 2011).

However, bio-based succinate still faces the challenge of becoming cost competitive against petrochemical-based alternatives. In order to develop the bio-based industrial production of succinic acid, it will be important to grow the cells in a low cost medium, and the working strain optimally should be able to metabolize a wide range of low-cost sugar feedstock to produce succinic acid in good yields so that the cheapest available raw materials can be used.

Sucrose is the major component of the residuals from cane, sorghum and sugar beet processing, although glucose, xylose, arabinose and other sugars are also present. Because sucrose is generally cheaper than glucose, it would be a less expensive carbon source and the residuals could be cost effectively used to grow bacteria to make succinate and other diacids.

Sucrose is a disaccharide composed of glucose and fructose and while there are a few *E. coli* strains naturally able to utilize sucrose, many cannot due to lack of an invertase to convert the sucrose to glucose and fructose. There are a few examples where sucrose has been used by *E. coli* to form a compound of industrial interest, however, the few reports to use sucrose also report slow fermentation or low yields of the desired product (Donnelly 2004; Lin 2005; Andersson 2007; Blankschien 2010).

Thus, what is needed in the art are better *E. coli* or other bacteria for producing feedstock chemicals that can efficiently utilize sucrose as a carbon source without sacrificing growth rates or yields. Preferably said strain would be able to use a number of low cost carbon sources and produce excellent yields of succinate and other small diacids, as discussed above.

SUMMARY OF THE INVENTION

We have modified our previously reported high yield *E. coli* succinate production strains such that they can now utilize sucrose as a carbon source. The results showed great potential for large-scale anaerobic production of succinate from sucrose based feedstocks. Two processes, aerobic or anaerobic fermentations, were developed to produce succinic acid from sucrose with a yield close to the maximum theoretical yields. Both processes were based on the modification of two basic strains by introducing genes (the five genes of the scr operon—scrABKYR) for both the uptake and utilization of sucrose.

Succinic acid production by the modified strains and parent strains were tested on fructose, sucrose, a mixture of glucose and fructose, a mixture of glucose, fructose and sucrose, and sucrose hydrolysis solution (partially acid hydrolyzed sucrose solution containing sucrose, glucose and fructose). The modified strains can produce succinic acid efficiently from all combinations of different carbon sources tested, with minimal byproduct formation and with high molar succinate yields close to that of the maximum theoretic values.

The molar succinic acid yield from fructose was the highest among the carbon sources tested. Using the mixture of glucose and fructose as the carbon source resulted in slightly lower yields and much higher productivity (rate) than using fructose alone. Fermenting sucrose mixed with fructose and glucose gave a 1.76-fold higher productivity than that when sucrose was used as the sole carbon source. Using sucrose pretreated with sulfuric acid as carbon source resulted in a similar succinic acid yield and productivity as that when using the mixture of sucrose, fructose, and glucose. The hydrolysis did not damage the product and gave a preparation that was as effectively fermented as the mixture of monomeric sugars.

The results of the effect of agitation rate in aerobic phase on succinate production showed that supplying large amount of oxygen in aerobic phase resulted in higher productions of formate and acetate, and therefore lower succinate yield. The low aeration experiment showed better succinate production with respect to yield, titer and volumetric productivity. This was most likely due to the period of microaerobiosis that the cells experienced before switching to a completely anaerobic environment. This microaerobic environment may have facilitated the cells to adjust their enzymatic machinery by expressing the proteins that were required in the anaerobic-production phase, making them a better biocatalyst for succinate production.

These studies suggests that fructose, sucrose, mixtures of glucose and fructose, mixtures of glucose, fructose and sucrose, or sucrose hydrolysis solution could be used for the economical and efficient production of succinic acid by our metabolically engineered E. coli strains. Thus, our modified strains have the potential to be used with a variety of low cost carbon sources.

As used herein "recombinant" is relating to, derived from, or containing genetically "engineered" material. In other words, the genome was intentionally manipulated in some way. The manipulation can use either native genes or genes from another species—all that is required is that the genome be intentionally modified in some way using various recombinant techniques.

"Overexpression" or "overexpressed" is defined herein to be at least 150% of protein activity as compared with an appropriate control species (where the parent lacks an activity altogether, it is assumed to be 1% to avoid dividing by zero). Overexpression can be achieved by mutating the protein to produce a more active form or a form that is resistant to inhibition, by removing inhibitors, or adding activators, and the like. Overexpression can also be achieved by removing repressors, adding multiple copies of the gene to the cell, or upregulating the endogenous gene, and the like. In a preferred embodiment, one or more expression vectors encoding the required protein(s) is/are added to the cell.

The terms "disruption" or "deactivated" or "reduced" (as their various grammatical forms) as used herein, refer to cell strains in which the native gene or promoter is mutated, deleted, interrupted, or down regulated in such a way as to decrease the activity of the gene at least 90% over the wild type un-disrupted gene. A gene or protein can be completely (100%) reduced by knockout or removal of the entire genomic DNA sequence. Use of a frame shift mutation, early stop codon, point mutations of critical residues, or deletions or insertions, and the like, can completely inactivate (100%) gene product by completely preventing transcription and/or translation of active protein.

Understanding the inherent degeneracy of the genetic code allows one of ordinary skill in the art to design multiple nucleotides that encode the same amino acid sequence. NCBI™ provides codon usage databases for optimizing DNA sequences for protein expression in various species. Using such databases, a gene or cDNA may be "optimized" for expression in E. coli, or other bacterial species using the codon bias for the species in which the gene will be expressed.

In calculating "% identity" the unaligned terminal portions of the query sequence are not included in the calculation. The identity is calculated over the entire length of the reference sequence, thus short local alignments with a query sequence are not relevant (e.g., % identity=number of aligned residues in the query sequence/length of reference sequence). Alignments are performed using BLAST homology alignment as described by Tatusova T A & Madden T L (1999) FEMS Microbiol. Lett. 174:247-250. The default parameters were used, except the filters were turned OFF. As of Jan. 1, 2001 the default parameters were as follows: BLASTN or BLASTP as appropriate; Matrix=none for BLASTN, BLOSUM62 for BLASTP; G Cost to open gap default=5 for nucleotides, 1 1 for proteins; E Cost to extend gap [Integer] default=2 for nucleotides, 1 for proteins; q Penalty for nucleotide mismatch [Integer] default=−3; r reward for nucleotide match [Integer] default=1; e expect value [Real] default=10; W word size [Integer] default=1 for nucleotides, 3 for proteins; y Dropoff (X) for blast extensions in bits (default if zero) default=20 for blastn, 7 for other programs; X dropoff value for gapped alignment (in bits) 30 for blastn, 15 for other programs; Z final X dropoff value for gapped alignment (in bits) 50 for blastn, 25 for other programs. This program is available online at NCBI™ (ncbi.nlm.nih.gov/BLAST/).

As used herein, the expressions "microorganism," "bacteria", "strain" and the like may be used interchangeably and all such designations include progeny. It is also understood that all progeny may not be precisely identical in DNA content, due to deliberate or inadvertent mutations added thereto. Mutant progeny that have the same function or biological activity as screened for in the originally transformed cell are included. Where distinct designations are intended, it will be clear from the context.

Reference to proteins herein can be understood to include reference to the gene encoding such protein, as appropriate. Thus, a claimed "permease" protein can include the related gene encoding that permease. However, it is preferred herein to refer to the protein by name, since the gene names in bacteria are largely meaningless and vary widely between species (e.g., the glucose permease gene in E. coli is ptsG). Where distinct meanings are intended (as in the claims), they will be referred to as "activities" or "proteins" or "genes."

The following abbreviations are used herein:

| ABBREVIA-TION | FULL NAME |
|---|---|
| 3PG | 3-Phosphoglyceraldehyde |
| AcCoA or A-coA | Acetyl CoA |
| aceBAK operon | Encodes genes required for the glyoxylate bypass and is essential for growth on acetate or fatty acids. Isocitrate |

-continued

| ABBREVIATION | FULL NAME |
|---|---|
| | lyase and malate synthase are encoded by aceA and aceB, respectively, while isocitrate dehydrogenase (IDH) kinase/phosphatase is encoded by aceK. |
| ackA | E. coli gene encoding ACK = acetate kinase |
| adhE | E. coli gene encoding ADH = alcohol dehydrogenase |
| AKG | Alpha-keto-glutarate |
| CmR | Chloramphenicol resistance gene |
| DO | Dissolved oxygen |
| EtOH | Ethanol |
| F1,6P | Fructose-1,6-diphosphate |
| F1P | Fructose-1-phosphate |
| F6P | Fructose-6-phosphate |
| FDH | Formate dehydrogenase, cofactor dependant |
| G6P | Glucose-6-phosphate |
| GAP | Glyceraldehyde phosphate |
| iclR | E. coli gene encoding ICLR aka aceBAK operon repressor |
| ICLR | The aceBAK operon repressor |
| LDH | lactate dehydrogenase |
| ldhA | E. coli gene encoding LDH, NAD+-dependent |
| MAL | Malate |
| OAA | Oxaloacetate |
| OD | Optical density of a sample (usually measured at a wavelength of 600 nm) |
| PEP | phosphoenolpyruvate |
| pepc | Gene encoding PEPC = phosphoenolpyruvate carboxylase |
| pta | E. coli gene encoding PTA = Phosphotransacetylase |
| pycA | Gene encoding PYC = Pyruvate carboxylase, preferably from Lactococcus lactis (Acc. No. AF068759) |
| PYR | Pyruvate |
| S6P | Sucrose-6-phosphate |
| scrA | Gene encoding Enzyme II(Scr) (45 kD) of the phosphoenolypyruvate-dependent phosphotransferase system (PTS) |
| scrB | Gene encoding sucrose 6-phosphate hydrolase (aka invertase) |
| scrK | Gene encoding intracellular and ATP-dependent fructokinase |
| Scr operon | Operon encoding sucrose uptake and utilization genes, preferably from S. typhimurium (Acc. No. X57400.1 (scrY); S96257.1 (scrK); X67750.1 (ScrABR)) |
| scrR | Gene encoding sucrose operon repressor, inactivated in the presence of sucrose, thus allowing expression of the scr operon |
| scrY | Gene encoding a sucrose porin |
| SUC | Succinate/succinic acid |
| TcR | Tetracycline resistance gene |
| ApR | Ampicillin resistance gene |
| ptsG | E. coli gene encoding glucose phophotransferase enzyme IIBC(Glc); aka glucose permease |
| sdhAB | E. coli gene encoding succinate dehydrogenase |
| poxB | E. coli gene encoding pyruvate dehydrogenase (aka pyruvate oxidase) |

DETAILED DESCRIPTION OF THE INVENTION

We have exemplified the invention using E. coli and genes from Lactococcus, E. coli, Salmonella or Clostridium. However, this was for convenience only because these genes or base mutants were already available, and the invention can be used with any bacteria having these same pathways and genes from any bacterial species provided that they catalyze the desired reactions. In fact, many such genes are already available in GenBank and other databases and can readily be employed herein. Enteric bacteria such as E. coli and others may be preferred in some circumstances due to familiarity with large scale culture of such bacteria, however, any bacteria that does not naturally use sucrose efficiently as a carbon source can be modified as described herein.

To find other genes that can be used in place of the genes herein, one need only search GenBank or other database with the protein sequence of interest. Once the protein has been found, it will be linked to a DNA sequence that can then be used to generate knockout or other vectors for manipulation of the endogenous gene, or to make an expression or other vector for the addition of heterologous genes. We have tested a number of proteins in this fashion, and confirm that the proteins are highly conserved and easily identified in a number of bacteria.

Of the sucrose utilization genes tested herein, the pUR400 derived set seemed to be more active in tests, but scr genes from *Clostriduium* were also tested and found to function.

The following examples are exemplary only and should not serve to unduly limit the invention.

EXAMPLE 1

Methodology

Strain construction—The host strains were constructed using the Datsenko and Wanner method (Datsenko and Wanner, 2000). In short, a linear DNA was constructed using PCR. The linear DNA contains 40 bases that are homologous to the upstream region of the gene of interest to be disrupted, the kanamycin resistance gene that is flanked with FRT sites, and 40 bases that are homologous to the other end of the gene of interest. The linear DNA was transformed into the *E. coli* strain, MG1655 carrying a lambda red expression plasmid (pKD46) and colonies containing the homologous recombination event are selected using Km resistance or another suitable resistance marker.

After selection, the Km resistance gene was eliminated by introducing a temperature sensitive plasmid pCP20, that expresses the FLP recombinase, which excises the Km cassettes bounded by FRT sites. The mutation was then verified using both PCR verification with appropriate primers and phenotype tests.

Combinations of mutations were made by transfer of the Km linked disruption by P1 transduction and subsequent removal of the Km marker as we have done before. We also have a number of strains with multiple mutations of key pathways from previous work and have obtained mutations with markers in individual genes proposed for deletion in this study.

Construction of plasmids—For purposes of placement of genes into one strain, the high-copy number plasmid pTrc99A (Pharmacia Corp.) that places the gene under control of the strong lactose-regulated lac promoter is frequently used as an initial vector. The multiple cloning site and lac screening property are useful attributes and we have used this extensively in the past in metabolic engineering studies. In case of testing two genes on different plasmids, we have used cloning into the multicloning region of the compatible origin plasmids of the pDHK series that have lac control and different drug markers. We have also used the p15A origin plasmids to provide compatible testing with two plasmids. More recently we have developed some equivalents of the pDUET plasmids having places where two separately induced genes can be expressed. Alternatives of the pBAD-TOPO series employing arabinose as an inducing agent have also been used and provide regulation of expression by an arabinose controlled promoter that has been shown to be well controlled under partial induction, has a wide range of inducible expression level and is suitable for use in a variety of media. Other options for controlled expression include the recent chromosomal integration of T7 promoter regulated genes with appropriate hosts and the phage attachment integration method. We thank Dr. K. Schmid (Universitat Osnabruck, Germany) for providing the *E. coli* K-12 strain containing the pUR400plasmid.

While plasmid introduction is useful as the initial test system, if the combination of genes becomes large, then integration strategies into the chromosome can be undertaken or larger constructs can be made using gene assembler technology such as ACEMBL or assembly in yeast cells via recombination of fragments.

Depending on the availability of existing plasmids expressing the genes, we will decide if the best approach is to clone the genes from chromosomal DNA of the organism or if DNA synthesis of the genes is the best route for plasmid construction. With the lowering of costs and improved reliability of long DNA synthesis by various vendors, this route is increasingly the most convenient and cost effective compared to the more traditional cloning/restriction enzyme based plasmid construction and we have implemented some synthetic constructs in our work. The method selected for a particular construction will depend on the on-hand molecules as well as the intricacy of the assembly. Recent published work in codon optimization, secondary mRNA structure or ribosome binding sites and other sequence considerations will be taken into account in designing the gene sequences for synthesis.

It is difficult to transform the pUR400 plasmid into *E. coli* due to its large size (70 kb), thus, conjugation was used to transfer the plasmid. Conjugation experiments were conducted at 37° C. in LB with the appropriate antibiotic(s). *E. coli* SBS550M containing the chloramphenicol resistance marker and *E. coli* K12 containing tetracycline marker were grown in 20 ml LB and incubated aerobically at 37° C. (250 rpm) to an OD600 of 0.4-0.6. To ensure that none of the resistance markers had been lost, 100 ml of each strain was plated on LB agar plates containing the appropriate antibiotic (*E. coli* K12: 35 mg/ml tetracycline; SBS550MG: 35 mg/ml chloramphenicol) and incubated overnight at 37° C. From the remaining culture, cells were mixed at a ratio of 1 ml K12 (donor strain): 9 ml SBS550MG (recipient strain) and incubated at 37° C. The conjugation mixture (100 ml of each) was diluted in sterilized water and serial dilutions were made, then the dilutions were plated on LB agar plates containing 35 mg/ml tetracycline and 35 mg/ml chloramphenicol. All plates were incubated at 37° C. Single colonies were restreaked on fresh plates to confirm antibiotic resistance. Next the SBS550MG pUR400strain was transformed with plasmid pHL413 carrying the *Lactococcus lactis* pycA gene. Single colonies were restreaked on plates containing the mixture of ampicillin (100 mg/ml) and tetracycline at a reduced concentration (20 mg/ml). Other bacteria used herein were made by similar techniques.

Strain characterization—Initial studies in shake flasks will be performed to evaluate the strains. The experimental set up will be similar to the methods we have used previously. The main focus of these sets of experiments is to test out the strains and to examine the effects of added overexpressed genes and host modifications on the production of the diacid. The concentration of diacid was determined by HPLC. These experiments will also provide feedback for further strain improvement by suggesting specific pathways to be engineered, e.g., to minimize byproducts or to increase needed cofactors.

When plasmids are used, the effect of host/plasmid interaction was minimized by comparing three different systems consisting of: the host only, a plasmid expressing biologically active enzyme, and a control system with the expression vector alone.

After the preliminary experiments with shake flasks, batch experiments were performed in well-controlled bioreactors. The main focus was to determine the performance of the constructed strain to produce the diacid under controlled environments.

The effect of genetic and environmental perturbations on metabolic and gene expression patterns was assessed by monitoring the extracellular metabolite concentrations, intermediate metabolite concentrations, and key enzymatic activities. Hexoses and fermentation products were measured by high-performance liquid chromatography (HPLC) using a specialized column. A Bio-Rad Aminex HXP-87H column specially designed for the analysis of small molecules was used.

Specifically, the fermentation products that can be quantified include the diacids to be studied, lactic acid, formic acid, acetic acid, pyruvate, glucose, and ethanol. Glucose, acetic acid and lactic acid can also be measured by commercially available enzymatic assays to supplement HPLC measurements. Hydrogen off-gas can be measured by GC chromatograph. The intracellular concentrations of CoA and acetyl-CoA can be measured by HPLC using a C-18 column and a UV detector. The NAD+/NADH levels can also be measured by HPLC. In experiments where a detailed analysis is desired, the activities of certain key enzymes in the metabolic pathways can also be measured.

Sucrose hydrolysis solution was made by mixing a 500 g/L sucrose solution with 0.01 (v/v) sulfuric acid and heated at temperatures of 100° C. for 30 min. The sucrose hydrolysate contained partially hydrolyzed sucrose and some glucose and fructose monomers and was cooled to room temperature and stored at 4° C. before use in the fermentation studies.

EXAMPLE 2

Test Strain

Figure 1:
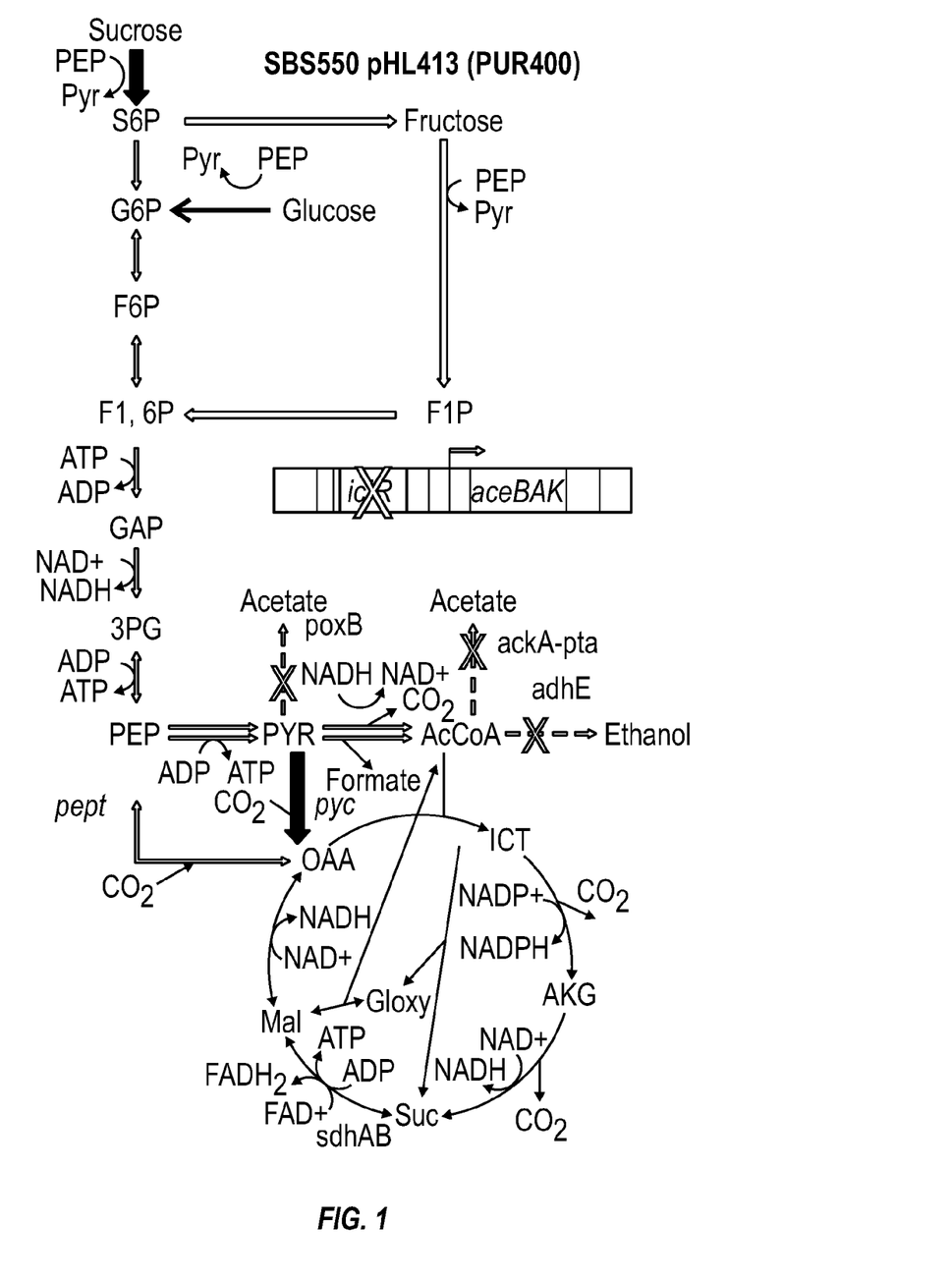
FIG. 1. Anaerobic glucose, fructose, and sucrose metabolism of SBS550MG pHL413 (ΔldhA, ΔadhE, ΔiclR, Δack-pta plus pyc$^+$) and SBS550MG pHL413 pUR400 (ΔldhA, ΔadhE, ΔiclR, Δack-pta plus pyc$^+$ plus scrKYABR$^+$) for high succinate production. The crosses (X) indicate gene or pathway inactivation. The bold arrows indicate an added sucrose pathway and added pycA gene from Lactococcus lactis.
Figure 2A:
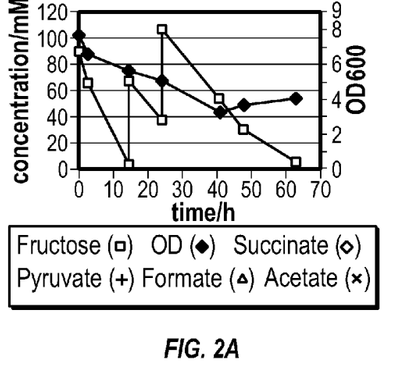
FIG. 2. Succinate production on prepared fructose solution by SBS550MG pHL413 (ΔldhA, ΔadhE, ΔiclR, Δack-pta plus pyc$^+$). Concentration of fructose and OD (a) and concentration of succinate and essential byproduct (b).
Figure 2B:
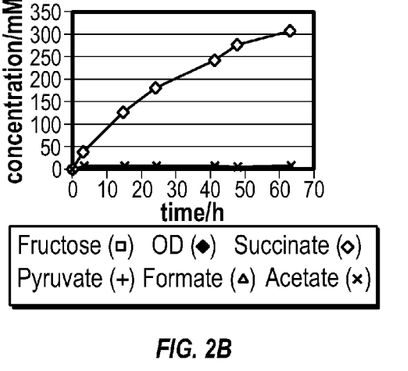
Figure 3A:
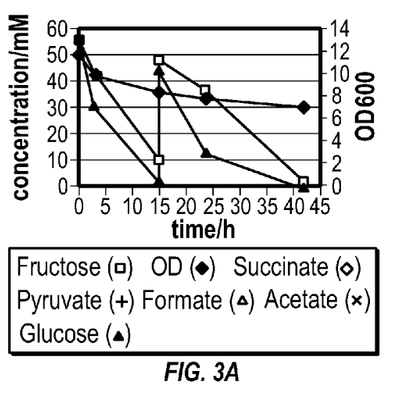
FIG. 3. Succinate production on the mixture of glucose and fructose by SBS550MG pHL413 (ΔldhA, ΔadhE, ΔiclR, Δack-pta plus pyc$^+$). Concentration of glucose and fructose and OD (a) and concentration of succinate and essential byproduct (b).
Figure 3B:
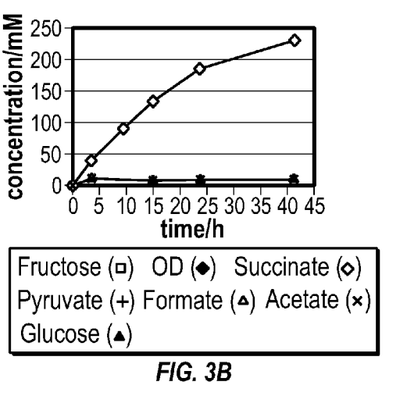
Figure 4A:
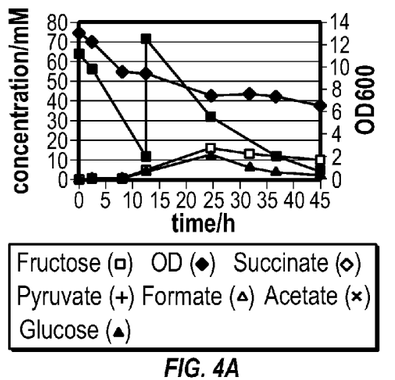
FIG. 4. Succinate production on sucrose by SBS550MG pHL413 pUR400 (ΔldhA, ΔadhE, ΔiclR, Δack-pta plus pyc$^+$ plus scrKYABR$^+$) strain. Concentration of sucrose and OD (a) and concentration of succinate and essential byproduct (b).
Figure 4B:
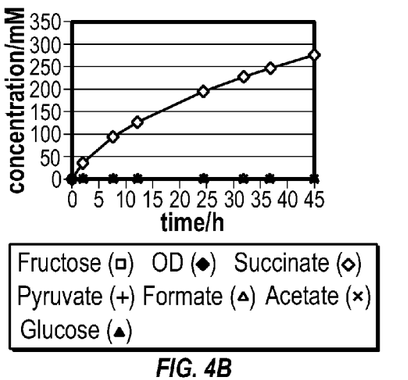
Figure 5A:
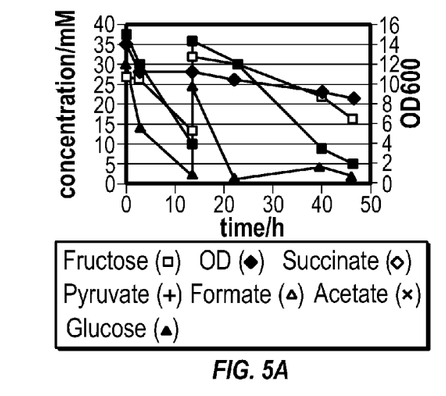
FIG. 5. Succinate production on a mixture of glucose, fructose, and sucrose by SBS550MG pHL413 pUR400 (ΔldhA, ΔadhE, ΔiclR, Δack-pta plus pyc$^+$ plus scrKYABR$^+$) strain. Concentration of sucrose and OD (a) and concentration of succinate and essential byproduct (b).
Figure 5B:
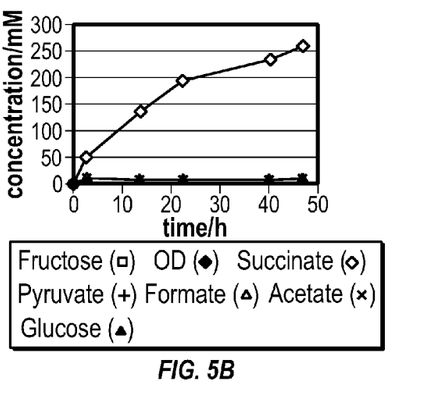
Figure 6A:
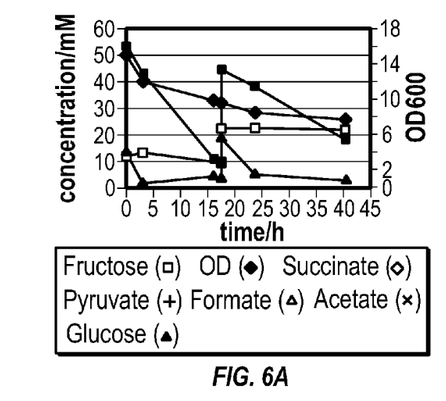
FIG. 6. Succinate production on sucrose hydrolysis solution by SBS550MG pHL413 pUR400 (ΔldhA, ΔadhE, ΔiclR, Δack-pta plus pyc$^+$ plus scrKYABR$^+$). Concentration of glucose, fructose and sucrose and OD (a) and concentration of succinate and essential byproduct (b).
Figure 6B:
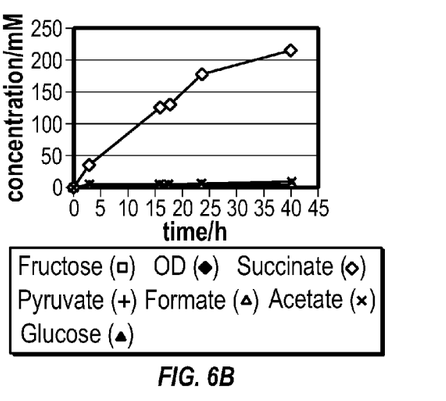
Figure 7A:
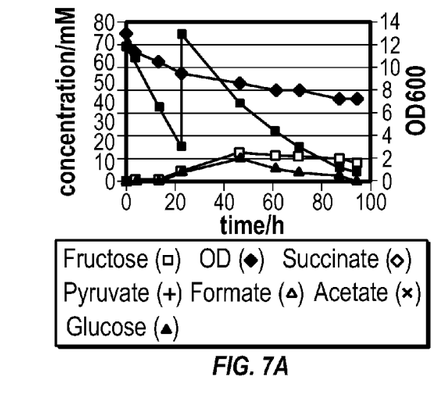
FIG. 7. Succinate production on sucrose by SBS550MG pHL413 (ΔldhA, ΔadhE, ΔiclR, Δack-pta plus pyc$^+$ plus scrKYABR$^+$) (stirring at 400 rpm). Concentration of sucrose and OD (a) and concentration of succinate and essential byproduct (b).
Figure 7B:
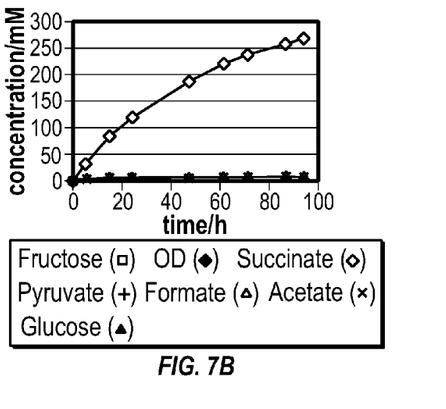
Figure 8A:
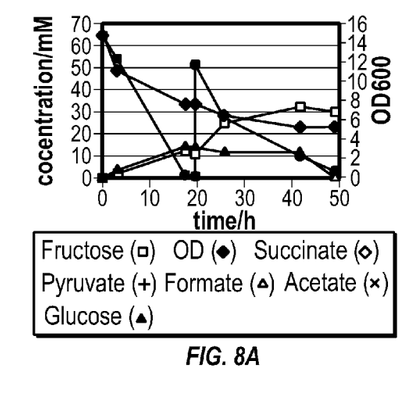
FIG. 8. Succinate production on sucrose by SBS550MG pHL413 pUR400 (ΔldhA, ΔadhE, ΔiclR, Δack-pta plus pyc$^+$ plus scrKYABR$^+$) (stirring at 800 rpm). Concentration of sucrose and OD (a) and concentration of succinate and essential byproduct (b).
Figure 8B:
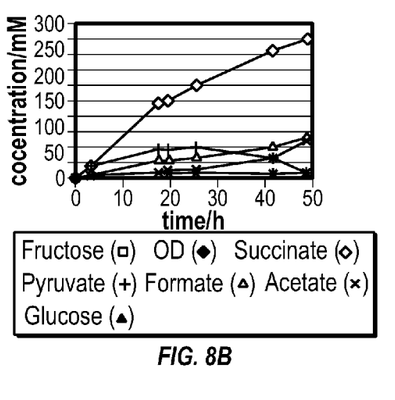

In order to quickly and easily demonstrate the usefuless of our invention, we added the scr operon for uptake and utilization of sucrose to *E. coli* strains that had already been designed to produce increased succinate. FIG. 1 shows the engineered pathways used in this example.

SBS550MG was previously created by disrupting adhE (alcohol dehydrogenase), ldhA (lactate dehydrogenase) and ack-pta (both acetate kinase and phosphotransacetylase were disrupted because these were already available, but either single disruption will suffice for the invention) from the central metabolic pathway and by activating the glyoxylate pathway through the inactivation of iclR, which encodes a transcriptional repressor protein of the glyoxylate bypass. The inactivation of these genes in SBS550MG increased the succinate yield from glucose to about 1.6 mol/mol with an average anaerobic productivity rate of 10 mM/h (approximately 0.64 mM/h-OD600). This strain is capable of fermenting high concentrations of glucose in less than 24 h.

Two plasmids were thus added to the above base strain. Plasmid pHL413 encodes the heterologous pyruvate carboxylase (pyc) from *Lactococcus lactis*. Plasmid pUR400 encodes the *Salmonella* scr operon, necessary for sucrose uptake and metabolism. Of course, it is also possible to combine these various genes into a single plasmid, or to insert the genes directly into the chromosome, but this method was quick and easy and serves as an excellent test system to prove the utility of the invention.

The scr operon contains five genes: scrA—coding for an EnzymeII(Scr) (45 kD) of the phosphoenolypyruvate-dependent phosphotransferase system (PTS), scrB—coding for a sucrose 6-phosphate hydrolase (invertase) (55 kD), scrK—coding for an intracellular and ATP-dependent fructokinase (39 kD), scrY—coding for a sucrose porin (58 kD) in the outer cell membrane, and scrR—a repressor. Additional details regarding plasmids and strains are shown in Table 1.

TABLE 1

List of strains and plasmids used in this study

| | Genotype | Reference |
|---|---|---|
| Strain | | |
| SBS550MG | ΔldhA, ΔadhE, ΔiclR, Δack-pta::Cm | Sánchez et al. (2005) |
| SBS550MG pHL413 | ΔldhA, ΔadhE, ΔiclR, Δack-pta::Cm plus pyc+ | |
| SBS550MG pUR400 | ΔldhA, ΔadhE, ΔiclR, Δack-pta::Cm plus scrKYABR+ Tc$^r$ | This study |
| SBS550MG pHL413 pUR400 | ΔldhA, ΔadhE, ΔiclR, Δack-pta::Cm plus pyc+ plus scrKYABR+ Tc$^r$ | This study |
| Plasmids | | |
| pHL413 | Pyruvate carboxylase from *L. lactis* cloned in pTrc99A, Ap$^R$ | Lin et al. 2004 |
| pUR400 | scrK, scrY, scrA, scrB and scrR genes from *Salmonella tryphimurium*, Tc$^r$ | Schmid K. 1988 |

Table 2 shows the results obtained using the strains of this example:

TABLE 2

Summary of fermentation parameters for SBS550MG pHL413 and SBS550MG pHL413 pUR400.

| Strain | Carbon source consumed (mM) | Agitation speed in aerobic phase (rpm) | Yield on sucrose$^a$ mol/mol | Yield on glucose$^b$ mol/mol | Productivity (g/L/h) | Specific productivity rate (g/L/h/OD)$^c$ |
|---|---|---|---|---|---|---|
| SBS550MG pHL413 pUR400 | Sucrose 110.17 | 400 | 3.33 | — | 0.46 | 0.055 |
| SBS550MG pHL413 pUR400 | Sucrose 124.35 | 500 | 3.15 | — | 0.48 | 0.047 |
| SBS550MG pHL413 pUR400 | Sucrose 120.18 | 800 | 2.05 | — | 0.60 | 0.058 |
| SBS550MG pHL413 | Fructose 245.54 | 500 | — | 1.86 | 0.82 | 0.150 |
| SBS550MG pHL413 | glucose/fructose 87.22/51.39 | 500 | — | 1.74 | 1.21 | 0.131 |
| SBS550MG pHL413 pUR400 | sucrose/glucose/fructose 60.00/52.49/27.13 | 500 | — | 1.67 | 0.85 | 0.079 |

TABLE 2-continued

Summary of fermentation parameters for SBS550MG pHL413 and SBS550MG pHL413 pUR400.

| Strain | Carbon source consumed (mM) | Agitation speed in aerobic phase (rpm) | Yield on sucrose[a] mol/mol | Yield on glucose[b] mol/mol | Productivity (g/L/h) | Specific productivity rate (g/L/h/OD)[c] |
|---|---|---|---|---|---|---|
| SBS550MG pHL413 pUR400 | Sucrose hydrolysis solution sucrose/glucose/fructose 73.70/27.87/−1.85 | 500 | — | 1.67 | 0.85 | 0.082 |

[a]The molar succinate yield was calculated as moles of succinate formed in the anaerobic phase divided by moles of the sucrose utilized (the residual hexose was lower than 10 mM for the 400 and 500 rpm experiments, and about 30 mM for the 800 rpm experiment).
[b]When hexose or sucrose/hexose mixtures were used as the carbon source the molar yield was based on hexose. One mole of sucrose equals two moles hexose.
[c]The specific succinate productivity during the anaerobic phase was calculated on the basis of the cell concentration or the amount of taking sample.

An examination of Table 2 shows that there was considerable variation in yields from different substrates. This observation suggests that the fluxes through different pathways are influenced by the nature of the substrate, including its entry point into central metabolism, as well as its oxidation state, which would lead to a different end product patterns.

Succinate yields were affected by the type of PTS-transportable sugar serving as the carbon source. Fructose is transported into the cell and phosphorylated to fructose-1-phosphate by a PEP-dependent phosphotransferase system. It then enters glycolysis after phosphorylation to fructose-1,6-bisphosphate. Sucrose-6-phosphate was identified as the primary product of the phosphoenolpyruvate (PEP)-dependent sucrose transport. Plasmid pUR400 mediates the "peripheral" metabolism of sucrose in E. coli K-12 by furnishing the sucrose-specific, membrane-bound compound EIISCR of the PTS and the hydrolyzing enzyme sucrose-6-phosphatehydrolase. The host contributes the general PTS proteins, including EI and HPr, an additional factor, EIIIglu, scr, which is required for the activity of the sucrose transport system. The primary intracellular product of sucrose-6-phosphate hydrolysis is fructose, which is converted to fructose-6-phosphate by an ATP-dependent kinase.

The highest succinate yields were observed with fructose as a carbon source as compared to glucose and sucrose for SBS550MG pHL413 and SBS550MG pHL413 pUR400. The succinate yields were roughly similar between the glucose/fructose mixture, the glucose/fructose/sucrose mixture, and the sucrose hydrolysis solution. However, SBS550MG pHL413 and SBS550MG pHL413 pUR400 showed large differences with respect to succinate productivity (rate of production) on the carbon sources glucose, fructose, and sucrose. Succinate productivity was much higher on glucose and fructose mixture as compared to other carbon sources, with sucrose allowing for the lowest succinate productivity. This shows the natural sucrose can be used as a carbon source, although succinate was produced more slowly than when using the free monomers. The choice of whether to use sucrose or a sucrose hydrolysis solution or free monomer would be an engineering and economic choice, depending on the availability and cost of these sugars.

The carbon source can influence the pattern of by-products formed. In this case, pyruvate, formate and acetate were still the major by-products. The concentration of each was low, but reduction of these by-products represents a further opportunity to increase yield.

Sucrose as a carbon source for E. coli has received little attention in the literature. The high yield and productivity of cells on a sucrose hydrolysis solution means that our modified bacteria have great potential to be used in industrial production processes. Furthermore, a wide range of confectionery, sugar cane, sorghum, sugar beet and other wastes are now accessible as possible carbon sources to produce succinate in bacteria.

EXAMPLE 3

Test Strain 2

Figure 9:
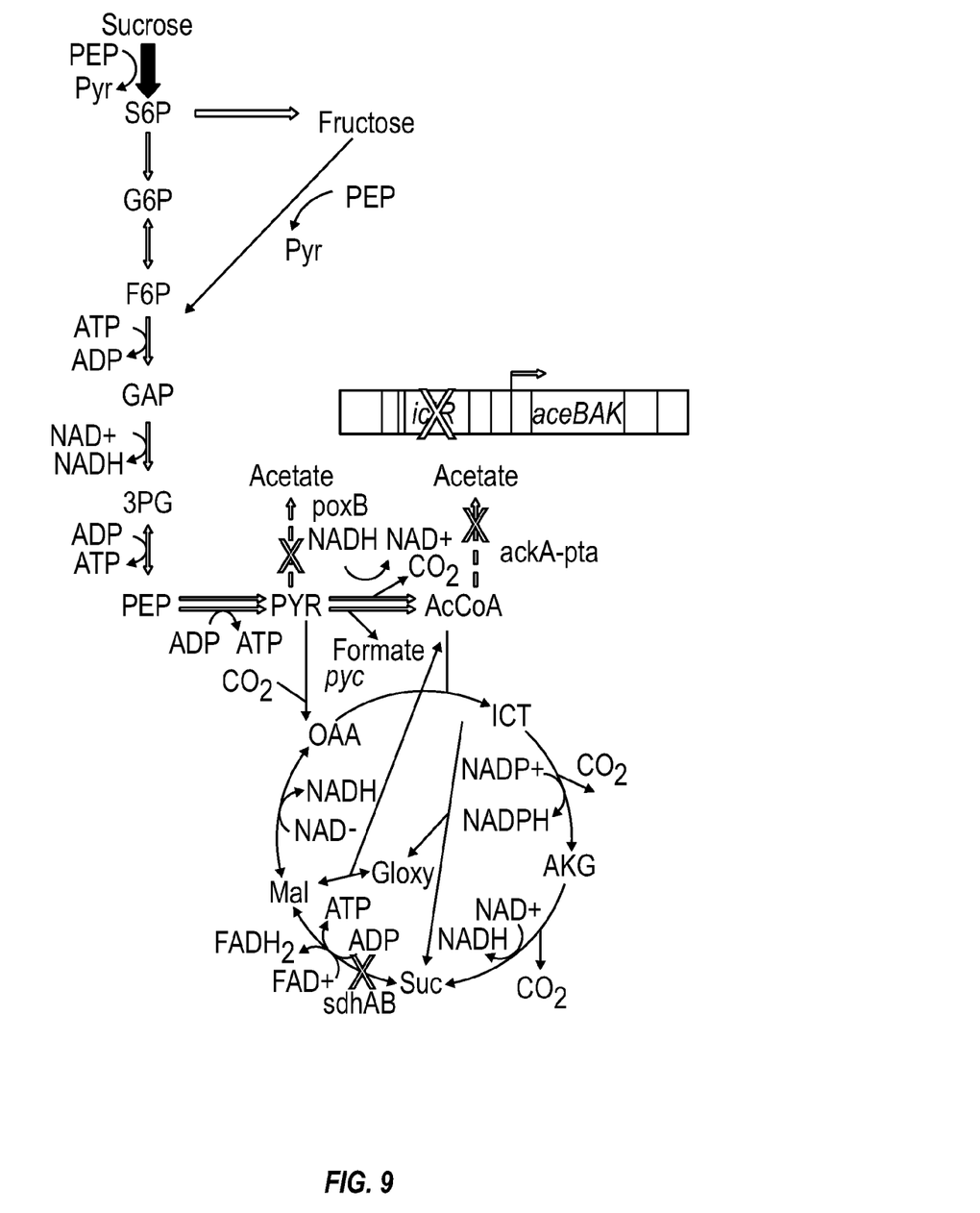
FIG. 9. Modified central aerobic metabolic pathway of HL27659 pHL413 pUR400 (ΔldhA, ΔadhE, ΔiclR, Δack-pta plus pyc$^+$ plus scrKYABR$^+$) for high aerobic succinate production. The crosses (X) indicate gene deactivation, the heavy arrow indicates the added sucrose pathway and grey arrow the added pyc$^+$ pathway.

We sought next to test the general applicability of our method by adding the scr operon to another succinate producing E. coli strain. For this, we used the already available strains HL2765k (ΔsdhAB, Δ (ackA-pta), ΔpoxB, ΔiclR) and HL27659k (ΔsdhAB, Δ(ackA-pta), ΔpoxB, ΔiclR, ΔptsG), which were constructed from GJT001 by Lin 2005. To these strains we added the same two plasmids as in Example 2. FIG. 9 shows the engineered pathways used in this example.

Table 3 lists the strains used in Example 3:

TABLE 3

List of strains and plasmids used in Example 3

| | Genotype | Reference |
|---|---|---|
| Strain | | |
| HL2765k | ΔsdhAB, Δ (ackA-pta), ΔpoxB, ΔiclR | Lin 2005 |
| HL27659k | ΔsdhAB, Δ (ackA-pta), ΔpoxB, ΔiclR, ΔptsG | Lin 2005 |
| HL2765k pHL413 | ΔsdhAB, Δ (ackA-pta), ΔpoxB, ΔiclR plus pyc[+] | |
| HL27659k pHL413 | ΔsdhAB, Δ (ackA-pta), ΔpoxB, ΔiclR, ΔptsG plus pyc[+] | |
| HL2765k pHL413 pUR400 | ΔsdhAB, Δ (ackA-pta), ΔpoxB, ΔiclR plus pyc[+] plus scrKYABR[+] | |
| HL27659k pHL413 PUR400 | ΔsdhAB, Δ (ackA-pta), ΔpoxB, ΔiclR, ΔptsG plus pyc[+] plus scrKYABR[+] | |
| Plasmids | | |
| pHL413 | Pyruvate carboxylase from L. lactis cloned in pTrc99A, Ap[R] | Lin 2004 |
| pUR400 | scrK, scrY, scrA, scrB and scrR genes, Tc[r] | Schmid 1988 |

The parent strains HL2765k and HL27659k were able to consume glucose and fructose as a carbon source, but not sucrose due to the lack of an invertase. Shake flask culture studies showed that the newly engineered strain containing the scr operon can now utilize sucrose. The strain HL2765k pUR400 and HL27659k pUR400 can produce succinate aerobically with a molar yield of 0.78±0.02 mol/mol and 1.35±0.13 mol/mol respectively.

Upon introduction of the second plasmid pHL413, which encodes the heterologous pyruvate carboxylase from Lacto-

*coccus lactis*, the molar succinate yield increased to 1.60±0.01 mol of succinate per mole of sucrose by the HL2765k pUR400 pHL413 strain and to 1.84±0.10 by the HL27659k pUR400 pHL413 strain.

In aerobic batch bioreactor studies, the succinate production rate was faster, and succinate production reached 101.83 mM with a yield of 1.90 when dissolved oxygen (DO) was controlled at 40±7% (by modifying the rpm of the stirrer). In addition, the results showed that dissolved oxygen had an important effect on succinate production by influencing pyruvate carboxylase (PYC) activity. This work demonstrates the possibility of producing succinate aerobically using sucrose as the carbon source.

Figures 10A, 10B:
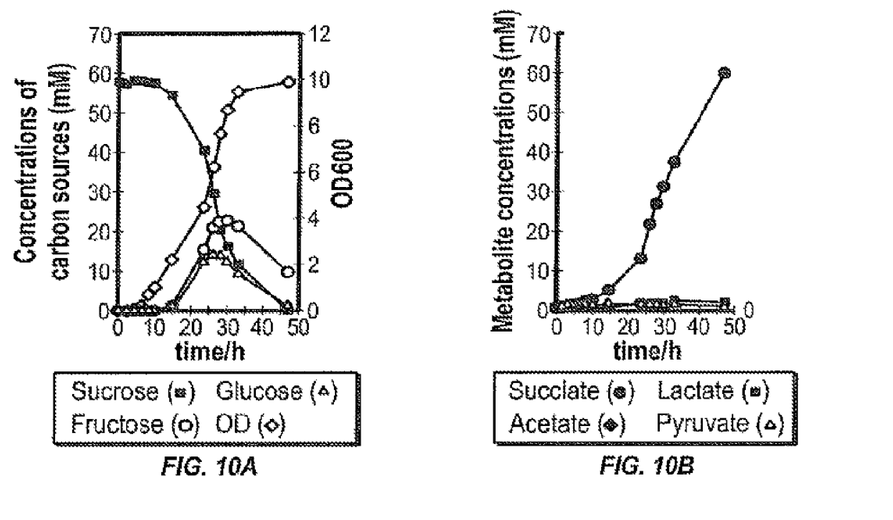
FIG. 10. Succinate production on sucrose by HL27659k pHL413pUR400 (ΔsdhAB, Δ (ackA-pta), ΔpoxB, ΔiclR, ΔptsG plus pyc$^+$ plus scrKYABR$^+$) grown in a bioreactor. (A) Concentrations of carbon source and OD. (B) Concentrations of succinate and other by-products.
Figure 11:
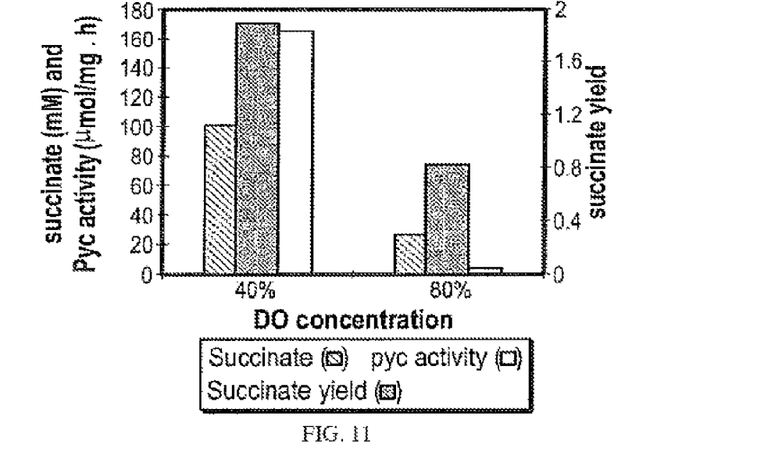
FIG. 11. DO effects on Succinate production and pycA activity by HL27659k pHL413pUR400 strain (ΔsdhAB, Δ (ackA-pta), ΔpoxB, ΔiclR, ΔptsG plus pyc$^+$ plus scrKYABR$^+$).

In more detail, these results are shown in Table 4 and FIGS. 10-11.

TABLE 4

Analysis of metabolic engineered *E. Coli* stains grown in shake flasks with sucrose

| Strain | Metabolite concentrations (mM) | | | | | Succinate yield |
|---|---|---|---|---|---|---|
|  | Glucose | Succinate | Formate | Acetate | Pyruvate |  |
| GJT001 pUR400 | 0.00 ± 0.00 | 0.25 ± 0.18 | 0.11 ± 0.19 | 18.02 ± 0.06 | 4.58 ± 0.08 | 0.01 ± 0.01 |
| HL2765k pUR400 | 15.47 ± 0.21 | 5.21 ± 0.13 | 0.05 ± 0.03 | 3.53 ± 0.05 | 22.40 ± 0.47 | 0.78 ± 0.02 |
| HL27659k pUR400 | 2.66 ± 1.40 | 12.61 ± 1.61 | 0.69 ± 0.24 | 9.03 ± 1.47 | 9.37 ± 3.27 | 1.35 ± 0.13 |
| HL2765k pHL413pUR400 | 0.00 ± 0.00 | 22.14 ± 2.69 | 0.44 ± 0.76 | 1.59 ± 0.17 | 3.50 ± 0.64 | 1.60 ± 0.11 |
| HL27659k pHL413pUR400 | 0.00 ± 0.00 | 24.00 ± 1.19 | 0.01 ± 0.01 | 1.32 ± 0.33 | 1.59 ± 0.77 | 1.84 ± 0.10 |

Concentrations shown here are from the 27 hour samples for GJT001 pUR400, HL2765k pUR400 and HL27659k pUR400, and 46 hour samples for HL2765k pHL413pUR400 and HL27659k pHL413pUR400 cultures. All the data are the average of measurements for triplicate cultures. The initial sucrose concentration was 30 mM.

Based on the above results obtained in aerobic shake flasks (not shown), batch fermentations of sucrose were also carried out with HL27659k pHL413pUR400 in 1-L stirred bioreactors. The results indicated that cell growth and metabolite production in stirred bioreactors were consistent with those in aerobic shake flasks except that cell growth and the production of succinic acid were higher in stirred bioreactor. Succinate production was 101.83 mM at 47 h with a molar yield of 1.90 on sucrose when the DO was controlled at 40±7%. Using a bioreactor generates higher productivity due to a more controlled environment. Cells grew to a maximum OD of 9.88, and 2.24 mM lactate and 2.68 mM acetate were accumulated as undesirable co-products after 47 hours (FIG. 10).

It was observed that in sucrose fermentation, free fructose or glucose in the media was not accumulated during the first 14 hours. This may due to the slow hydrolysis of sucrose. It was shown that the concentrations of glucose and fructose in the media increased rapidly as the concentration of sucrose dropped sharply. This suggests that the hydrolysis of sucrose was faster than the consumption of glucose and fructose during the exponential phase. Glucose accumulation reached a maximum of 14.67 mM at 26 h. After that, the cells consumed the glucose along with the remaining sucrose. Fructose accumulation reached a maximum of 22.82 mM at 30 h when glucose had already been consumed. These results indicate that when HL27659k pHL413 pUR400 was fermented on sucrose, glucose was utilized preferentially to fructose due to catabolite repression (FIG. 10).

Additionally, DO was an important factor for succinate production and yield. HL27659k pHL413 pUR400 showed higher succinate production and yield when the DO was controlled between 20±7% and 40±7% (data not shown) than when DO was controlled at 80±7%. When the DO was at 80±7%, HL27659k pHL413 pUR400 produced 26.07 mM succinate with a yield of 0.80 on sucrose. The activity of pyruvate carboxylase was only 3.39 µmol·mg$^{-1}$·min$^{-1}$ when the DO was controlled at 80±7% and it was 165.10 µmol·mg$^{-1}$·min$^{-1}$ when culture was grown under a DO of 40±7% (FIG. 11). High DO during the entire growth phase may reduce the activity of pyruvate carboxylase which resulted in a large accumulation of pyruvate (65.14 mM) and acetate (14.30 mM). The sucrose utilization rate was also lower under this condition. These results indicate that to optimize yield, the strains should be grown under moderate aeration (20-40% dissolved oxygen).

Although further improvements are still required, such as simplifying the double plasmid system and optimizing culture conditions to make the current system feasible in large scale applications, the current study demonstrated that *E. coli* strains can be engineered to produce succinate from sucrose under aerobic conditions, which can be a base for further improvements.

Aerobic cell culture conditions have many advantages over anaerobic conditions that favor implementation on an industrial scale due to healthier cells, faster 10 carbon throughput and product formation. In this study, we demonstrated that *E. coli* HL27659k pHL413 pUR400 strain can grow and produce succinate on sucrose. This may lead to potential opportunities to produce succinate from sucrose aerobically in the industry. Alternatively, the cells can be grown aerobically for a time to build cell mass, slowly switched to anaerobic conditions over about an hour (0.5-1.5 hr), and then grown anaerobically until the products are harvested.

The following publications are incorporated by reference in their entirety herein.

Andersson, C., et al. (2007) Effect of different carbon sources on the production of succinic acid using metabolically engineered *Escherichia coli*, Biotechnol. Prog. 23: 381-388.

Blankschien, M. D., et al. (2010) Metabolic engineering of *Escherichia coli* for the production of succinate from glycerol, Metab. Eng. 12: 409-419.

Cox, S. J. (2006) Development of a metabolic network design and optimization frame work incorporating implementation constraints: A succinate production case study, Metab. Eng. 8: 46-57.

Datsenko, K A, B L Wanner (2000) One-step inactivation of chromosomal genes in *Escherichia coli* K-12 using PCR products. Proc. Natl. Acad. Sci. U.S.A. 97(12):6640-5.

D. W. Penfold and L. E Macaskie (2004) Production of H2 from sucrose by *Escherichia coli* strains carrying the pUR400 plasmid, which encodes invertase activity, Biotechnology Letters 26(24): 1879-1883.

Donnelly M. I., et al. (2004) Method to produce succinic acid from raw hydrolysates, U.S. Pat. No. 6,743,610.

Guettler M. V., et al. (1996) Method for making succinic acid, bacterial variants for use in the process, and methods for obtaining variants, U.S. Pat. No. 5,573,931.

Isar, J., et al. (2007) A statistical approach to study the interactive effects of process parameters on succinic acid production from *Bacteroides fragilis*. Anaerobe13: 50-56.

Lee, P. C., et al. (2003) Batch and continuous cultures of *Mannheimia succiniciproducens* MBEL55E for the production of succinic acid from whey and corn steep liquor. Bioprocess Biosyst. Eng. 26: 63-67.

Lin, H., et al. (2004) Increasing the acetyl-CoA pool in the presence of overexpressed phosphoenolpyruvate carboxylase or pyruvate carboxylase enhances succinate production in *Escherichia coli*, Biotechnol. Prog. 20: 1599-1604.

Henry Lin, et al. (2005) Chemostat culture characterization of *Escherichia coli* mutant strains metabolically engineered for aerobic succinate production: a study of the modified metabolic network based on metabolite profile, enzyme activity, and gene expression profile. Metabolic Engineering 7(5-6): 337-352.

Okino, S., et al. (2005) Production of organic acids by *Corynebacterium glutamicum* under oxygen deprivation. Appl. Microbiol. Biotechnol. 68: 475-480.

Raab, A. M. et al. (2010) Metabolic engineering of *Saccharomyces cerevisiae* for the biotechnological production of succinic acid, Metab. Eng. 12: 518-525.

Samuelov, N. S., et al. (1991) Influence of CO2-HCO3+ levels and pH on growth, succinate production and enzyme activities of *Anaerobiospirillum succiniciproducens*, Appl. Environ. Microbiol. 57: 3013-3019.

Sanchez, A. M., et al. (2005a) Efficient succinate production from glucose through overexpression of pyruvate carboxylase in an *Escherichia coli* alcohol dehydrogenase and lactate dehydrogenase mutant, Biotechnol. Prog. 21: 358-365.

Sanchez, A. M., et al. (2005b) Novel pathway engineering design of the anaerobic central metabolic pathway in *E. coli* to increase succinate yield and productivity, Metab. Eng. 7: 229-239.

Sanchez, A. M., et al. (2006) Batch culture characterization and metabolic flux analysis of succinate producing *Escherichia coli* strains, Metab. Eng. 8: 209-226.

Schmid K, et al. (1988) Plasmid mediated sucrose metabolism in *Escherichia coli* K-12: Mapping of the scr genes of pUR400. Mol Microbiol. 2: 1-8.

Singh, A., et al. (2011) Manipulating redox and ATP balancing for improved production of succinate in *E. coli*, Metab. Eng. 13: 76-81.

Wang, J., et al. (2011) Succinate production from different carbon sources under anaerobic conditions by metabolic engineered *Escherichia coli* strains, Metabolic Engineering 13: 328-335.

U.S. Pat. Nos. 7,569,380, 7,790,416, WO2008030995, U.S. Pat. Nos. 7,935,511, 7,927,859, US2006073577 et seq.

We claim:

1. A recombinant *E. coli* bacteria, comprising
   a. an overexpressed pyruvate carboxylase (pyc) activity,
   b. an added overexpressed scr operon containing scrA, scrB, scrK and scrY and scrR activities,
   c. deactivated acetate kinase (ack) or phosphotransacetylase (pta) or both ack-pta genes,
   d. deactivated repressor of aceBAK operon (iclR) genes, and
      i. deactivated alcohol dehydrogenase (adhE) and lactate dehydrogenase (ldhA) genes, or
      ii. deactivated succinate dehydrogenase (sdhAB), pyruvate oxidase (poxB) genes and optionally deactivated glucose permease (ptsG) genes;
   wherein said bacteria produce at least 1.9 moles of succinate per mole of sucrose carbon source when said bacteria are grown aerobically for a period of time at 40% ±7% $O_2$.

2. The recombinant bacteria of claim 1, comprising ΔldhA, ΔadhE, ΔiclR, Δack-pta, plus pyc+, plus scrKYABR+.

3. The recombinant bacteria of claim 1, comprising ΔsdhAB, Δack-pta, ΔpoxB, ΔiclR, plus pyc+ plus scrKYABR+.

4. The recombinant bacteria of claim 1, comprising ΔsdhAB, Δack-pta, ΔpoxB, ΔiclR, ΔptsG plus pyc+ plus scrKYABR+.

5. A recombinant *E. coli* bacteria, comprising an overexpressed pyruvate carboxylase (pyc) activity, plus overexpressed scrK, scrY scrA, scrB, and scrR activities, wherein said bacteria produce at least 1.9 moles of succinate per mole of sucrose carbon source when said bacteria are grown aerobically for a period of time at 40% ±7% $O_2$.

6. A recombinant *E. coli* bacteria, comprising an overexpressed pyruvate carboxylase (pyc) activities, plus an overexpressed scrK, scrY scrA, scrB, and scrR activities, plus reduced acetate kinase (ack) or phosphotransacetylase (pta) or both ack-pta activities, and reduced repressor of aceBAK operon (iclR) activity, wherein said bacteria produce at least 1.9 moles of succinate per mole of sucrose carbon source when said bacteria are grown aerobically for a period of time at 40% ±7% $O_2$.

7. A recombinant *E. coli* bacteria, comprising overexpressed scrA, scrB, scrK, scrY and scrR activities, plus deactivated acetate kinase (ack) or phosphotransacetylase (pta) or both ack-pta activities, and reduced repressor of aceBAK operon (iclR) activity, wherein said bacteria produce at least 1.9 moles of succinate per mole of sucrose carbon source when said bacteria are grown aerobically for a period of time at 40%±7% $O_2$.

8. A recombinant bacteria, comprising:
   a. an overexpressed pyruvate carboxylase (pyc),
   b. exogenous scrA, scrB, scrK, scrY and scrR activities,
   c. reduced acetate kinase or phosphotransacetylase or both activities,
   d. reduced repressor of aceBAK operon activity, and
      i. reduced alcohol dehydrogenase and lactate dehydrogenase activity, or
      ii. reduced succinate dehydrogenase, pyruvate oxidase activities and optionally reduced glucose permease activity,
   said recombinant bacteria being able to metabolize sucrose and being made from a parent bacteria that is unable to metabolize sucrose without the addition of exogenous scrA, scrB, scrK, scrY and scrR activities to said parent bacteria;
   wherein said bacteria produce at least 3.15 moles of succinate per mole of sucrose carbon source when said bacteria are grown aerobically for a period of time at 20-40% $O_2$, then switched to anaerobic conditions over the course of about an hour and said succinate is harvested after at least 12 hours growth under anaerobic conditions.

9. A recombinant bacteria, comprising:
   a. an overexpressed pyruvate carboxylase (pyc),
   b. exogenous scrA, scrB, scrK, scrY and scrR genes from *Salmonella*,
   c. reduced acetate kinase or phosphotransacetylase or both activities, d. reduced repressor of aceBAK operon activity, and
  i. reduced alcohol dehydrogenase and lactate dehydrogenase activity, or
  ii. reduced succinate dehydrogenase, pyruvate oxidase activities and optionally reduced glucose permease activity,
said recombinant bacteria being able to grow by metabolizing sucrose and being made from a parent bacteria that is unable to metabolize sucrose without the addition of exogenous scrA, scrB, scrK, scrY and scrR genes to said parent bacteria:,
wherein said bacteria produce at least 1.9 moles of succinate per mole of sucrose carbon source when said bacteria are grown aerobically for a period of time at 40%±7% $O_2$.

10. A method of making a dicarboxylic acid, said method comprising culturing the bacteria of claim 1 in a medium comprising sucrose as a carbon source for sufficient time to produce a dicarboxylic acid, and harvesting said dicarboxylic acid.

11. A method of making succinic acid, said method comprising culturing the bacteria of claim 1 in a medium comprising sucrose as a carbon source for sufficient time to produce succinic acid, and harvesting said succinic acid.

12. The method of claim 10, wherein the cells are grown aerobically.

13. The method of claim 11, wherein the cells are grown aerobically.

14. The method of claim 10, wherein the cells are grown anaerobically.

15. The method of claim 11, wherein the cells are grown anaerobically.

16. The method of claim 10, wherein the cells are grown aerobically for a period of time, then switched to anaerobic conditions over the course of about an hour.

17. The method of claim 11, wherein the cells are grown aerobically for a period of time, then switched to anaerobic conditions over the course of about an hour.

\* \* \* \* \*